United States Patent [19]

Bauman

[11] Patent Number: 4,552,847
[45] Date of Patent: Nov. 12, 1985

[54] VISUAL QUALITY CONTROL METHOD FOR BARRIER TREATED CONTAINERS

[75] Inventor: Bernard D. Bauman, Coopersburg, Pa.

[73] Assignee: Air Products and Chemicals, Inc., Allentown, Pa.

[21] Appl. No.: 536,602

[22] Filed: Sep. 28, 1983

[51] Int. Cl.$^4$ ............... G01N 15/08; G01N 33/44
[52] U.S. Cl. ........................... 136/5; 73/38; 436/85
[58] Field of Search ............ 436/5.85; 73/38; 350/36

[56] References Cited

U.S. PATENT DOCUMENTS

| | | | |
|---|---|---|---|
| 2,079,925 | 5/1937 | Reichert | 73/150 |
| 2,639,617 | 5/1953 | Larkin et al. | 73/432 |
| 2,811,468 | 10/1957 | Joffre | 117/95 |
| 2,963,349 | 12/1960 | Bernard et al. | 23/230 |
| 3,672,842 | 6/1972 | Florin | 23/230 R |
| 3,862,284 | 1/1975 | Dixon et al. | 264/83 |
| 3,963,442 | 6/1976 | Bullard et al. | 23/253 TP |
| 3,988,491 | 10/1976 | Dixon et al. | 428/288 |
| 4,116,634 | 9/1978 | Nieberlein | 436/5 |
| 4,209,367 | 6/1980 | Seko et al. | 204/296 X |
| 4,296,151 | 10/1981 | Boultinghouse | 427/255.1 |

OTHER PUBLICATIONS

*Plastics Technology*, 6/79, pp. 61–64.
"The Science and Technology of Appearance Measurement," Hunter Lab., *Plastics & Rubber Processing*, 3/79, pp. 10–16.
*Modern Plastics*, 11/77, pp. 34–37.
Estimation of the Effective Permeability of Thin Surface Layers Created by Exposure of Polyethylene to Fluorine, Keros et al., Polym. Eng. & Sci., Aug. 1982, vol. 22, No. 12, 738–46.

*Primary Examiner*—Barry S. Richman
*Assistant Examiner*—C. M. Delahunty
*Attorney, Agent, or Firm*—Richard A. Dannells, Jr.; James C. Simmons; E. Eugene Innis

[57] ABSTRACT

A method is provided for distinguishing between a solid surface or object treated by exposure to a reactive gas to have a measurable impermeability to a nonpolar fluid and a surface or object permeable to the fluid by the steps of:

(a) contacting the surface or object being tested with a dilute solution of crystal violet for a fixed period of time,
(b) separating the surface or object from contact with crystal violet solution and
(c) making a visual or instrumental determination of the extent to which crystal violet has adhered to and/or penetrated into the surface or object.

10 Claims, 2 Drawing Figures

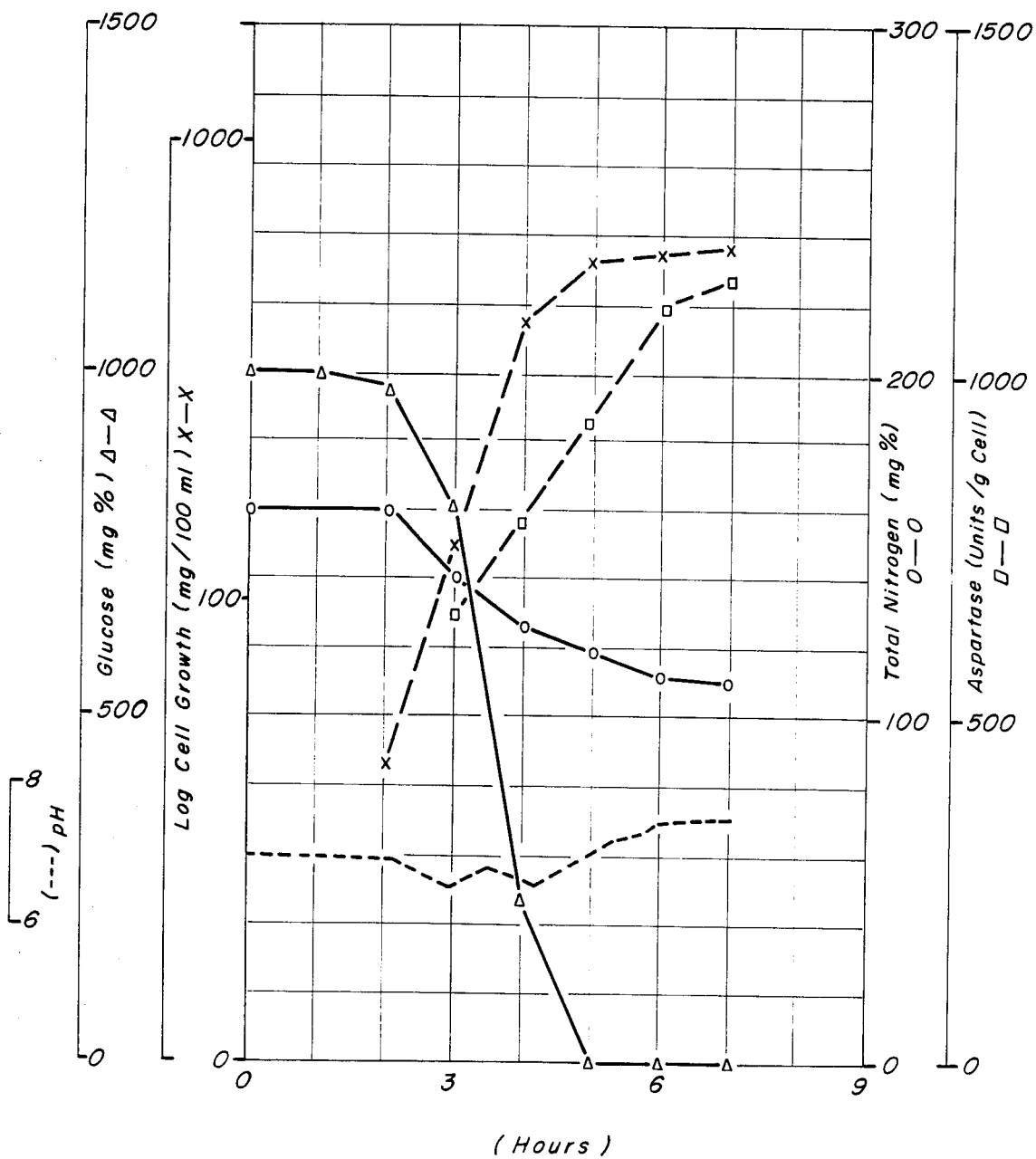
Growth Characteristics Of B. Subtilis Strain Asp-4

4,552,847

VISUAL QUALITY CONTROL METHOD FOR BARRIER TREATED CONTAINERS

DESCRIPTION

1. Technical Field

This invention relates to a quality control method for determining the degree of impermeability of barrier-treated solid polymers toward volatile materials. More particularly, it relates to a method for determining whether articles such as containers have been successfully treated to a condition of impermeability toward hydrocarbon liquids.

2. Background Art

The use of blow molded thermoplastic containers and other hollow articles has become commercially significant as disclosed, for example, in the article "Blow Molding: The Next Five Years," *Plastics Technology, (June,* 1979), pages 61-64. Blow molding is a process which make possible construction of intricately shaped, lightweight, corrosion-resistant containers, which have high mechanical strength. Containers made from thermoplastic resins can be used for the storage of aqueous or highly polar liquids and, for this purpose, are essentially impervious to the substances stored therein. However, blow molded thermoplastic containers are not entirely satisfactory for the storage of relatively nonvolatile nonpolar organic liquids because the organic liquids can difuse through the wall of the thermoplastic container at an unacceptably high rate.

It would be highly desirable to be able to use blow molded thermoplastic containers for safe and long-term storage of commercially significant nonpolar solvents, including gasoline and other liquid fuels, hydrocarbon-based cleaning fluids or household solvents and oil-based paints containing hydrocarbon solvents. In presently available thermoplastic containers, diffusion of hydrocarbon solvents through the walls thereof often leads to an unacceptable loss of at least part of the solvent material contained therein. As a result, the properties of the stored materials, for example, oil-based paint, may change so drastically as to become useless. It will also be apparent that blow molded containers for hydrocarbon fluids, e.g. gasoline tanks, have met with limited commercial acceptance, owing to the loss of fuel therefrom. In the case of presently available thermoplastic containers, nonpolar liquids, especially hydrocarbons, can diffuse through the container to some extent. This diffusion of hydrocarbon fuel from containers can contribute to air pollution.

Thermoplastic resins which can be blow molded include polymers and copolymers of styrene, acrylonitrile, vinyl chloride and olefins containing at least one aliphatic mono-1-olefin having a maximum of 8 carbon atoms. The preferred types of materials for blow molded containers are, however, polyolefins, that is, homopolymers and copolymers of ethylene, propylene, 1-butene, 1-pentene, 4-methyl-1-pentene, 3-methyl-1-butene, 3,3-dimethyl-1-butene and the like.

Attempts to overcome the tendency of volatile nonpolar organic solvents to diffuse through the walls of blow molded thermoplastic containers have included treating the surfaces of the containers both during and after the blow molding process.

One representative post-treatment method for providing a barrier layer on the surface of a polyolefin object and making blow molded polyolefin containers relatively impermeable to nonpolar solvents has been proposed by Joffre in U.S. Pat. No. 2,811,468. In this process, the internal surface of a blow molded bottle is fluorinated with pure fluorine or with a mixture of fluorine and air/nitrogen. The fluorinated containers thus have much better barrier properties toward hydrocarbon solvents than untreated containers. The barrier properties were determined by testing with allyl caproate, a volatile, highly odoriferous material. However, even accelerated testing requires a long period of time and can not, in a practical sense, be used for testing every container in a batch of treated containers.

A more effective and economical way of obtaining blow molded containers, having enhanced barrier properties to hydrocarbon solvents, is proposed by Dixon et al. in U.S. Pat. No. 3,862,284. Dixon et al. teach that, in the blow molding of thermoplastic materials, 0.1-10% by volume of fluorine and 99.9-90% by volume of an inert gas are blended into a fluid medium before expanding the parison of the container to the contour of the mold. Containers produced by this process, using the AIROPAK ® system, have an interior surface which is extremely resistant to permeation by nonpolar organic solvents. See, for example, "Fluorination of Polyolefin Container During Blow Molding to Reduce Solvent Permeation," *Plastics and Rubber Processing,* (March, 1979), pages 10-16.

Another approach to the problem of enhancing the barrier properties of blow-molded containers, known as the Dow sulfonation process, employs posttreatment of the container with a mixture of sulfur trioxide and nitrogen or dry air. In a second step, the container is treated with ammonia and a dry diluent gas. This technique is considered in an article, "Industrial Blow Molding: The Sleeping Giant Stirs," *Modern Plastics,* (November, 1977), pages 34-37.

Other treated polymeric material which may need to be tested include the types disclosed by Dixon et al. in U.S. Pat. No. 3,988,491 and by Boultinghouse in U.S. Pat. No. 4,296,151.

One method for evaluation of solvent retention of surface fluorinated thermoplastics, as disclosed by Dixon et al. '284, is measuring gross loss of weight from toluene-containing bottles, kept at 100° F., for various periods of time. Another method comprises filling treated containers with motor oil, placing the filled bottles on filter paper and determining the time required for the oil to penetrate through the container to the filter paper. As is the case of testing with allyl caproate, these techniques are too slow to be acceptable in commercial practice and do not lend themselves to testing each container, for example, each fuel tank, coming off a molding machine.

Quality control in the manufacture of barrier-coated thermoplastic containers is accordingly limited by the lack of a rapid, inexpensive method to determine the efficacy of the surface treatment in decreasing solvent loss by permeation through the walls of the container. Any practically useful test for barrier properties must be rapid so as to detect variations in product properties very rapidly, so that immediate corrective action can be taken.

The tests described above are typical of method which directly measure permeability of solvent through the walls of the container. Indirect methods, which measure properties other than permeability, but which can be related to permeability, can also be used. However, methods which destroy the container can not be used for testing every container coming from a blow molding line. When the containers are large, e.g., 55-gallon high density polyethylene (HDPE) drums or gasoline tanks, destructive testing methods would lead to an economically unacceptable loss of materials.

One direct method is determining permeability is the pressure-accelerated permeability method, in which a sample is cut from a treated container and mounted in a high pressure test cell. Liquid or gas is forced through the wall of the container by diffusion under high pressure. The material diffusing through the wall can be detected by physical or chemical means. This method is less than optimum because it is a destructive quality control test and because days or weeks may be required for determining the permeability of a particular sample.

Attempts have been made to measure permeability directly by exposing the inner surface of barrier-coated thermoplastic material, or a sample cut from the product, to a solution of an intensely colored or fluorescent dye, removing the solution after a preset period of time and determining the degree and depth of dye penetration into the walls of the product visually or instrumentally. This method is limited to products free of interfering dark colored and/or opaque pigments and is generally unreliable even for evaluating appropriate types of samples.

The use of total reflectance and contact angle measurements is also unreliable. Multiple internal reflectance (MIR) measurements, using Fourier transform analysis, are reliable but very complex.

Available indirect tests for effectiveness of surface treatment include chemical or physical detection of the active component in the barrier layer, for example, fluorine in the AIROPAK ® system. When fluorine is used as the treating material, X-ray fluorescence, electron spectroscopy for chemical analysis (ESCA), or combustion, followed by chemical analysis, can be used. The ESCA technique employs low energy X-rays, which dislodge core electrons of molecules near the surface of the specimen being analyzed, and therefore permits specific analysis for elements at the surface of the sample.

Because these methods test only small portions of the treated surface, they frequently fail to detect containers with unacceptable barrier properties, because a given surface may have been treated in a non-uniform fashion. Optical and physical property determinations are also highly sensitive to contamination and, in some cases, difficult to correlate with barrier properties. These methods, like methods determining permeability directly, are generally slow and tedious and too expensive to permit obtaining permeability data on all containers coming from a production line.

The use of dyes in visual tests for surface properties of materials is disclosed, for example, in U.S. Patents by Reichert (2,079,925), Larkin (2,639,617), Bernard et al. (2,963,349), Florin (3,672,842) and Bullard et al. (3,963,442). None of these references addresses the application of a dye or stain to a thermoplastic surface or object, treated to decrease permeability toward nonpolar solvents.

It is accordingly the object of this invention to provide a rapid, qualitative method, which correlates readily with surface permeability of treated thermoplastics and which can, if desired, be used for testing representative samples, or all containers, coming from a blow molding production line.

DISCLOSURE OF THE INVENTION

This invention relates to a method for determining whether a solid surface or object, treated by exposure to a reactive gas, has become measurably impermeable toward a nonpolar fluid, and comprises the steps of:
(a) leaving the surface or object in contact with a dilute solution of crystal violet,
(b) removing the surface or object from contact with the crystal violet solution and
(c) making a determination of whether crystal violet has adhered to or penetrated into the surface or object being tested.

Although a variety of dyes or stains was evaluated for substantivity toward fluorine-treated surfaces, it was surprisingly found that closely related dyes behaved in markedly differing fashion. Of dyes evaluated, only crystal violet, methyl violet and acridine orange were taken up or held on any of the samples, fluorinated or unfluorinated. Crystal violet alone permitted differentation of fluorine-treated samples from untreated controls. Accordingly, crystal violet is highly specific for indicating sufficient fluorine exposure of a thermoplastic substrate to impart impermeability.

In the practice of this invention, the crystal violet is conveniently brought into contact with the surface or article being tested in the form of a dilute aqueous solution. The amount of crystal violet in solution can be as low as 0.001% by weight. A practical upper limit is of the order of 1% by weight. Solutions of 0.05–0.25% are preferred, most preferably about 0.1% by weight.

If the presence of crystal violet is unobjectionable in the intended final use of the object being tested, for example, 55-gallon drums for hydrocarbon solvents or fuel tanks, each object coming off a blow molding line can be tested.

It is preferred that articles, being tested in accordance with invention, have surfaces of thermoplastic materials, treated with aqueous fluorine.

The article or surface being tested should be exposed to the solution of crystal violet for a minimum of about 1 second. Long exposures, longer than about 15 seconds appear to be unnecessary. Therefore, exposure of the article being tested to crystal violet solution for 5–15 seconds is preferred.

The materials, or samples of articles, being tested can be immersed in the crystal violet solution for the requisite time. When the insides of containers are being tested, the container can be partially filled with dilute crystal violet solution and shaken or swirled to permit exposure of the surface to the crystal violet solution. Then the crystal violet solution can be poured out of the container.

Testing is done at about ambient temperatures, that is, from 10°–30° C., and can be done on the factory floor, rather than at a remote testing facility.

After the sample has been removed from contact with the crystal violet solution, the article or surface being tested is preferably washed with running tap water and dried in air. When the article being tested is a container, it can be drained dry, washed with portions of tap water and drained dry again.

Among materials tested in accordance with this invention, preferred materials are polyolefins, more preferably ethylene polymers or copolymers.

Although the mechanisms by which this invention operate are not completely understood, it is thought that fluorine provides sites for dye receptivity and that high fluorination correlates with high dye receptivity. It is not completely certain whether adsorption or penetration of dye is the primary mechansim involved. Accordingly, "adherence/penetration," as used in the specification and claims, is intended to include adsorption, adherence and penetration and to be correlated with the "blueness" of the treated sample, whether "blueness" is determined visually or instrumentally.

The measurement of "blueness" and other color attributes is described more fully in "The Science and Technology of Appearance Measurement," Hunter Lab. Essentially, in visual examination of a color, neither its spectroscopic curve nor a separate response of the viewer's eyes to red, green and blue light receptors, in fact occurs. What is perceived is hue. Hue is correspondingly attributed to whether the object being viewed is red, orange, yellow, green, blue or violet. It will be understood that it is acceptable, and preferred, to make empirical correlations between "blueness" and long-term permeability behavior of thermoplastic specimens treated in any particular fashion.

Visual determinations can be made by comparison with color standards comprising previously-dyed, acceptably fluorinated or otherwise-treated samples of a selected polymer substrate. More quantitatively, the use of a reflectance colorimeter calibrated with a graph relating barrier properties to colorimetic measurement, can be employed.

BEST MODE FOR CARRYING OUT THE INVENTION

Figure 1:
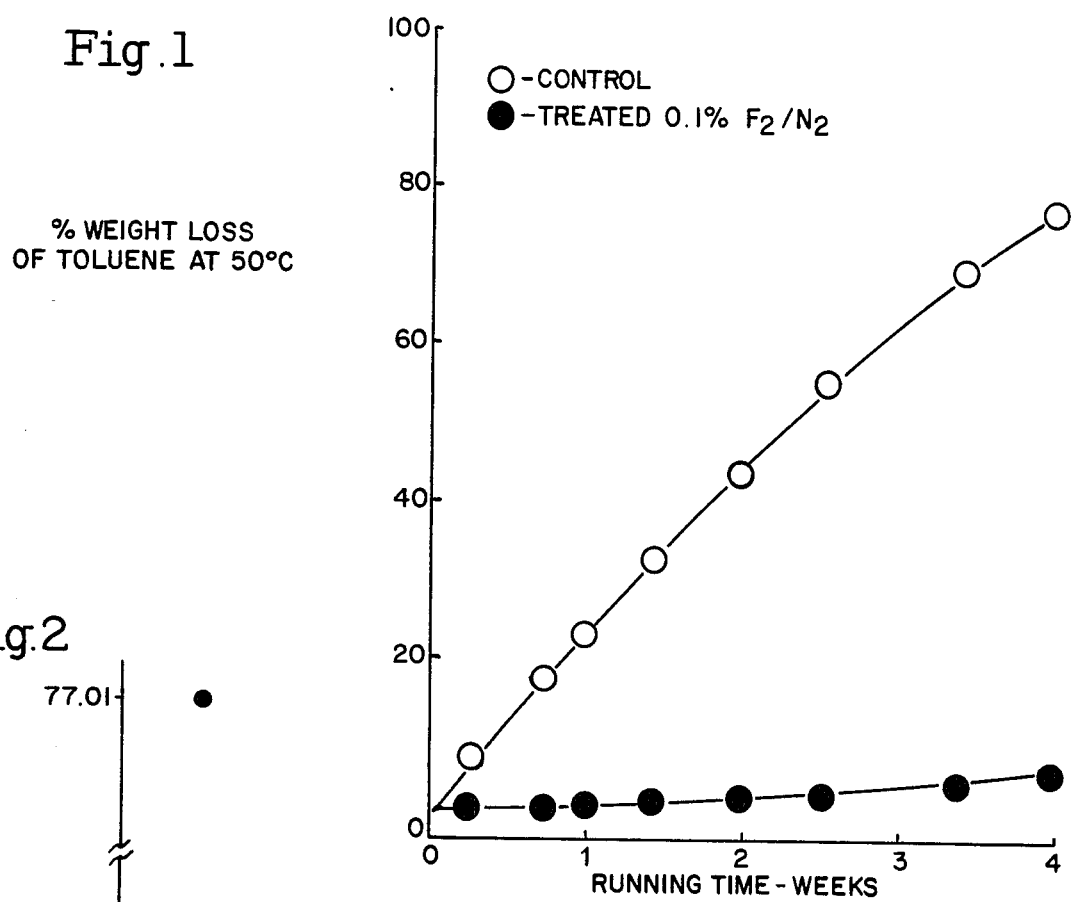
In FIG. 1 is shown weight loss of treated and untreated bottles, containing toluene at 50° C.

In most preferred aspects, the method of the invention will be done at about ambient temperature, the dilute solution of crystal violet will be aqueous and will be kept in contact with the surface or object being tested for 5-15 seconds. The test method is most preferably utilized with polyolefin substrates, particularly ethylene polymers or copolymers, most especially those treated by fluorination.

Without further elaboration it is believed that one skilled in the art can, using the preceding description, utilize the present invention to its fullest extent. The following specific embodiments are, therefore, to be construed as merely illustrative and not limitative of the remainder of the disclosure in any way whatsoever. In the following Examples, the temperatures are set forth uncorrected in degrees Celsius. Unless otherwise, indicated, all parts and percentages are by weight.

EXAMPLE 1

Samples from polyethylene bottles treated by the process of Dixon et al., U.S. Pat. No. 3,862,284 (2% fluorine and 98% nitrogen by volume) or treated with nitrogen during blow molding (control) were screened for dye sensitivity. Each dye or stain was used in the form of an aqueous solution (0.1% by weight). A sample was immersed in the dye solution at room temperature for ten seconds, rinsed with tap water and dried in air at room temperature. Results of visual determination of color uptake are given in Table 1.

Of the various dyes or stains tested, only crystal violet, methyl violet and acridine orange were taken up and held on either the fluorinated samples or on the controls. Of these, only crystal violet permitted differentiation between the fluorinated and the unfluorinated sample. Accordingly, cryatal violet is a direct visual indicator for fluorine-treated polyethylene.

EXAMPLE 2

(a) Bottles (16-ounce size), blow molded from Marlex ® polyethylene (high load melt index=10) by the method of Dixon et al., '284, weighed about 30 grams and had a minimum wall thickness of about 0.025 inch. Samples obtained at various $N_2/F_2$ ratios (0.1-2.0% $F_2$) were tared, filled with toluene and reweighed. The bottles were placed in a constant temperature oven (50° C.) and weighed at intervals for 28 days. The oven was blanketed with nitrogen to prevent the gas composition within the oven from moving into the explosive limits for toluene. The project was carried out under a hood to prevent buildup of toluene fumes.

TABLE 1

| Dye/stain | Structure | Dye Uptake Control | Dye Uptake Fluorinated |
|---|---|---|---|
| Methyl orange | $Me_2N-\langle\bigcirc\rangle-N=N-\langle\bigcirc\rangle-SO_3Na$ | no | no |
| Metanil yellow | $SO_3Na-\langle\bigcirc\rangle-N=N-\langle\bigcirc\rangle-NH-\langle\bigcirc\rangle$ | no | no |

TABLE 1-continued

| Dye/stain | Structure | Dye Uptake Control | Dye Uptake Fluorinated |
|---|---|---|---|
| Crystal violet | [structure] | no | yes |
| Titan yellow | A—N=N—NH—A, A = [structure] | no | no |
| Methyl thymol blue | [structure], B = (NaO$_2$CCH$_2$)$_2$NCH$_2$— | no | no |
| Basic fuchsin | [structure] | no | no |
| Alizarin Red S | [structure] ·H$_2$O | no | no |
| N,N—Dimethyl-p-phenylene-diamine·HCl | Me$_2$NC$_6$H$_4$NH$_2$·2HCl | no | no |
| Methyl red | [structure] | no | no |

TABLE 1-continued

| Dye/stain | Structure | Dye Uptake Control | Fluorinated |
|---|---|---|---|
| Malachite green | [structure shown] | no | no |
| Methyl violet | [structure shown] | yes | yes |
| Acridine orange | [structure shown] | slight | slight |

Percent weight loss of solvent after a given interval is:

$$\% \text{ loss} = \frac{[(Y - X) - (Z - X)]}{(Y - X)} \times 100\%$$

wherein
X = tare weight of capped bottle
Y = initial weight (day 0) of capped, solvent-filled bottle
Z = weight of bottle on subsequent days.

The total loss over the selected testing period used Z, determined for the final day of that period. Permeation curves were obtained by plotting the total percentage weight loss against the running time of the testing period. The change in the rate of solvent weight loss was apparent from a change in the slope of the permeation curve.

As shown in FIG. 1, polyethylene bottles treated with 0.1% $F_2$ in $N_2$ displayed almost no loss of toluene at 50° C. during a month of testing.

From empirical data obtained by accelerated testing at 50° C., predictions as to weight loss on storage for extended periods, e.g. a year, at room temperature (23° C.), have been made.

Figure 2:
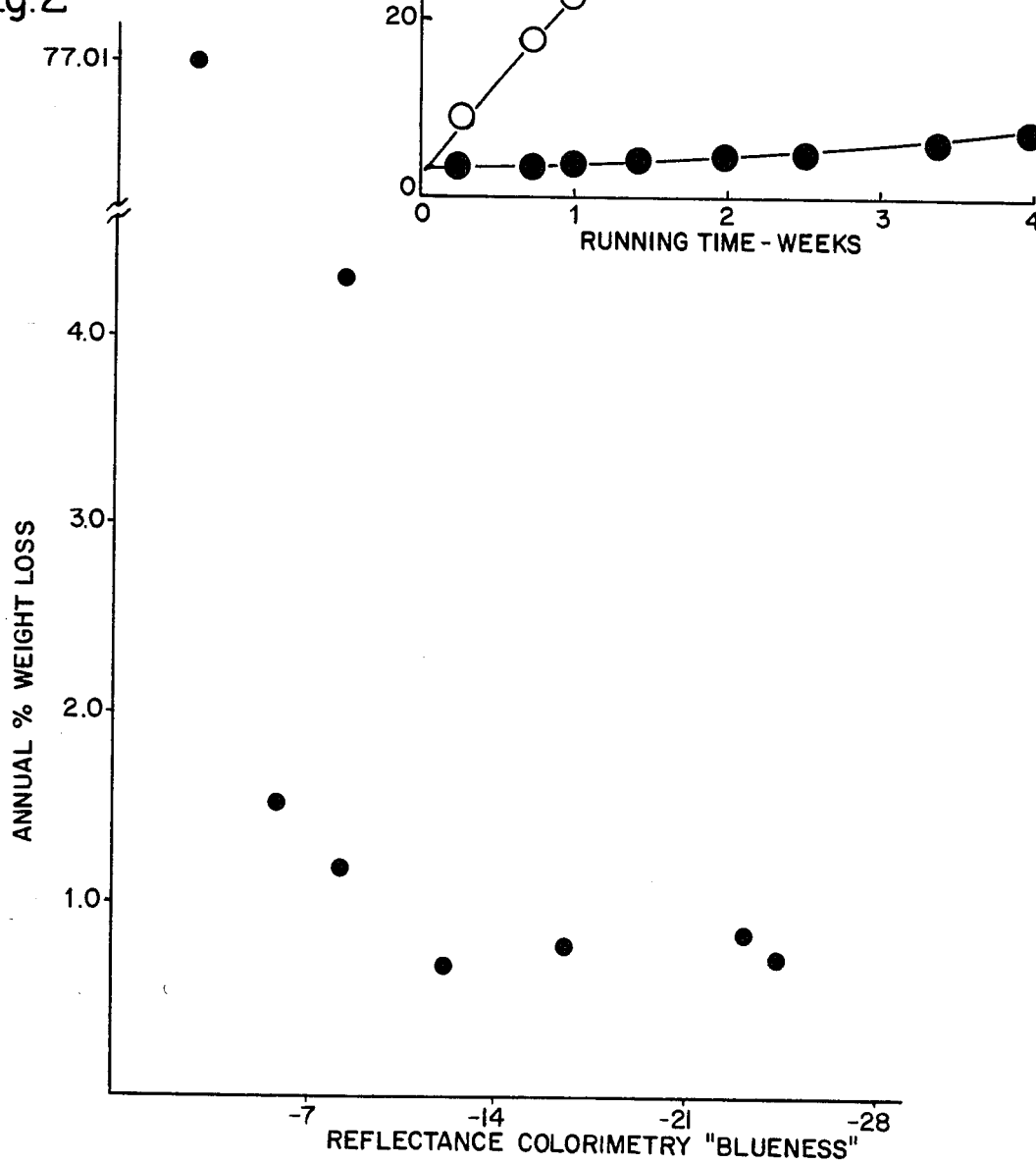
In FIG. 2 is shown a correlation between the "blueness" of samples treated with crystal violet and the long-term permeability of these surfaces toward a typical volatile nonpolar fluid.

(b) Samples from fluorine-treated polyethylene containers were immersed in an aqueous solution (0.1% by weight) of crystal violet at room temperature for 10 seconds. After the sample was removed from the crystal violer solution and washed under running tap water for 20 seconds, it was allowed to dry in air for two minutes and was examined by reflectance colorimetry using a Hunter Lab D-25 reflectance colorimeter for determination of "blueness" or absorption at 450 nm. The "blueness" measured in this fashion was plotted against annual percent of weight loss, determined as in Example 2(a). These data are shown in FIG. 2. Accordingly, the "blueness" determined by reflectance colorimetry is directly correlated to annual percent of weight loss through treated polyethylene and is an index of permeability.

EXAMPLE 3

Samples of fluorinated polyethylene, treated by the Dixon et al. process as in Examples 1 and 2, were immersed in 0.1% crystal violet solution for various periods of time, rinsed under running tap water, dried and evaluated as in Example 2(b). It was found that immersion in the dye solution for more than about 5 seconds did not increase resulting "blueness" of the samples. Accordingly, for 0.1% dye solutions, 5 seconds' immersion will give reproducible results.

EXAMPLE 4

A 55-gallon drum, blow molded from polyethylene and treated with fluorine as above, is partially filled with a dilute solution (about 0.1% by weight) of crystal violet. The container is shaken for several seconds, whereupon the crystal violet solution is poured out. The emptied container is washed several times with small portions of tap water and viewed visually for homogeneity of blue color.

This method permits determination of non-uniformity in a large surface-treated object.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

I claim:

1. A method for qualitatively distinguishing between a solid surface or object, which has been treated by exposure to fluorine gas, to have a measurably reduced level of permeability to a nonpolar fluid relative to a surface or object not treated with fluorine, comprising the steps of:
   (a) exposing the surface or object being tested to a dilute solution of crystal violet for a fixed period of time,
   (b) separating the surface or object being tested from the crystal violet solution and
   (c) observing visually or instrumentally the extent to which the crystal violet has adhered to or penetrated into the surface or object, whereby uptake of the crystal violet indicates the measurably reduced level of permeability.

2. The method of claim 1, wherein the dilute solution of crystal violet is aqueous.

3. The method of claim 1, carried out at about ambient temperature.

4. The method of claim 1, wherein the surface or object being tested is exposed to the dilute crystal violet solution for at least about 1 second.

5. The method of claim 1, wherein the crystal violet solution is aqueous and contains about 0.1% by weight of crystal violet.

6. The method of claim 1, wherein the surface or object being tested is made of polyolefin.

7. The method of claim 1, wherein the surface or object being tested is made of an ethylene polymer or copolymer.

8. The method of claim 1, wherein testing is done at about ambient temperature, the dilute solution of crystal violet is aqueous and the surface or object being tested is exposed to the dilute crystal violet solution for about 5-15 seconds.

9. The method of claim 1, wherein testing is done at about ambient temperature, the solution of crystal violet solution is aqueous, the surface or object being tested is exposed to the dilute crystal violet solution for about 5-15 seconds and the surface or object being tested is made of polyolefin.

10. The method of claim 1, wherein testing is done at about ambient temperature, the dilute solution of crystal violet is aqueous, the surface or object being tested is exposed to the dilute crystal violet solution for about 5-15 seconds and the surface or object being tested is made of an ethylene polymer or copolymer.

11. The method of claim 1, including the further step of washing the surface or object being tested with water and drying in air after separating the surface or object from the crystal violet solution and before observing visually or instrumentally the extent to which crystal violet has adhered to or penetrated into the surface or object.

12. The method of claim 11, wherein the surface or object being tested is exposed to the dilute crystal violet solution for about 5-15 seconds.

* * * * *